United States Patent
McQuillen et al.

(10) Patent No.: US 9,664,132 B2
(45) Date of Patent: May 30, 2017

(54) OXYGEN SENSOR CONTROL RESPONSIVE TO RESISTANCE AND IMPEDANCE

(71) Applicant: Ford Global Technologies, LLC, Dearborn, MI (US)

(72) Inventors: Michael McQuillen, Warren, MI (US); Gopichandra Surnilla, West Bloomfield, MI (US); Richard E. Soltis, Saline, MI (US); Daniel A. Makled, Dearborn, MI (US); Stephen B. Smith, Livonia, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 208 days.

(21) Appl. No.: 14/568,916

(22) Filed: Dec. 12, 2014

(65) Prior Publication Data
US 2016/0169138 A1  Jun. 16, 2016

(51) Int. Cl.
| | | |
|---|---|---|
| *H05B 1/02* | (2006.01) | |
| *F02D 41/14* | (2006.01) | |
| *G01N 33/00* | (2006.01) | |
| *G01N 27/16* | (2006.01) | |
| *F02D 41/24* | (2006.01) | |
| *G01N 27/406* | (2006.01) | |

(52) U.S. Cl.
CPC ..... *F02D 41/1494* (2013.01); *F02D 41/2474* (2013.01); *G01N 27/16* (2013.01); *G01N 33/0039* (2013.01); *G01N 27/4067* (2013.01)

(58) Field of Classification Search
CPC F02D 41/1494; G01N 33/0039; G01N 27/16; H05B 1/0236; H05B 1/02; H05B 3/0042
USPC .............. 219/202, 205, 206, 494, 497, 505; 123/689
See application file for complete search history.

(56) References Cited

U.S. PATENT DOCUMENTS

| | | | |
|---|---|---|---|
| 4,720,993 A | 1/1988 | Badwal | |
| 5,645,746 A * | 7/1997 | Walsh | B60R 16/0207 219/203 |
| 5,852,228 A | 12/1998 | Yamashita et al. | |
| 6,082,345 A * | 7/2000 | Ikeuchi | F02D 41/1494 123/688 |
| 6,492,629 B1 * | 12/2002 | Sopory | H05B 1/0205 219/485 |
| 6,651,315 B1 * | 11/2003 | Graves | H01C 1/14 29/612 |
| 6,723,965 B2 | 4/2004 | Ohkuma et al. | |
| 7,189,948 B2 | 3/2007 | Kwon et al. | |

(Continued)

OTHER PUBLICATIONS

McQuillen, Michael et al., "Oxygen Sensor Control Based on Water Contact," U.S. Appl. No. 14/542,181, filed Nov. 14, 2014, 50 pages.

*Primary Examiner* — Mark Paschall
(74) *Attorney, Agent, or Firm* — Julia Voutyras; McCoy Russell LLP

(57) ABSTRACT

Various methods are provided for operating an oxygen sensor. In one example, a method of operating an oxygen sensor including a heater comprises sampling a first heater resistance at a first temperature, and determining a resistance-temperature transfer function relating heater resistance to heater temperature based on the first heater resistance and a second heater resistance at a second temperature, the second temperature different from the first temperature.

19 Claims, 6 Drawing Sheets

(56) References Cited

U.S. PATENT DOCUMENTS

| | | |
|---|---|---|
| 8,407,986 B2 | 4/2013 | Hahn |
| 8,888,361 B2* | 11/2014 | Ooishi ................. G01K 17/006 374/147 |
| 2003/0019865 A1 | 1/2003 | Whitney et al. |
| 2003/0039299 A1* | 2/2003 | Horovitz .............. G01N 27/123 374/141 |
| 2006/0027012 A1 | 2/2006 | Allmendinger |
| 2007/0007134 A1 | 1/2007 | Kawase et al. |
| 2010/0000984 A1 | 1/2010 | Aoki et al. |
| 2011/0314893 A1 | 12/2011 | Masui |
| 2012/0097553 A1* | 4/2012 | Classen .............. G01N 27/4175 205/781 |
| 2013/0133399 A1 | 5/2013 | Hibino |
| 2014/0013819 A1 | 1/2014 | Kawaguchi et al. |
| 2014/0076741 A1 | 3/2014 | Adams |
| 2014/0121948 A1 | 5/2014 | Marlett et al. |
| 2015/0114086 A1* | 4/2015 | Lin .................... G01N 15/0656 73/28.01 |

* cited by examiner

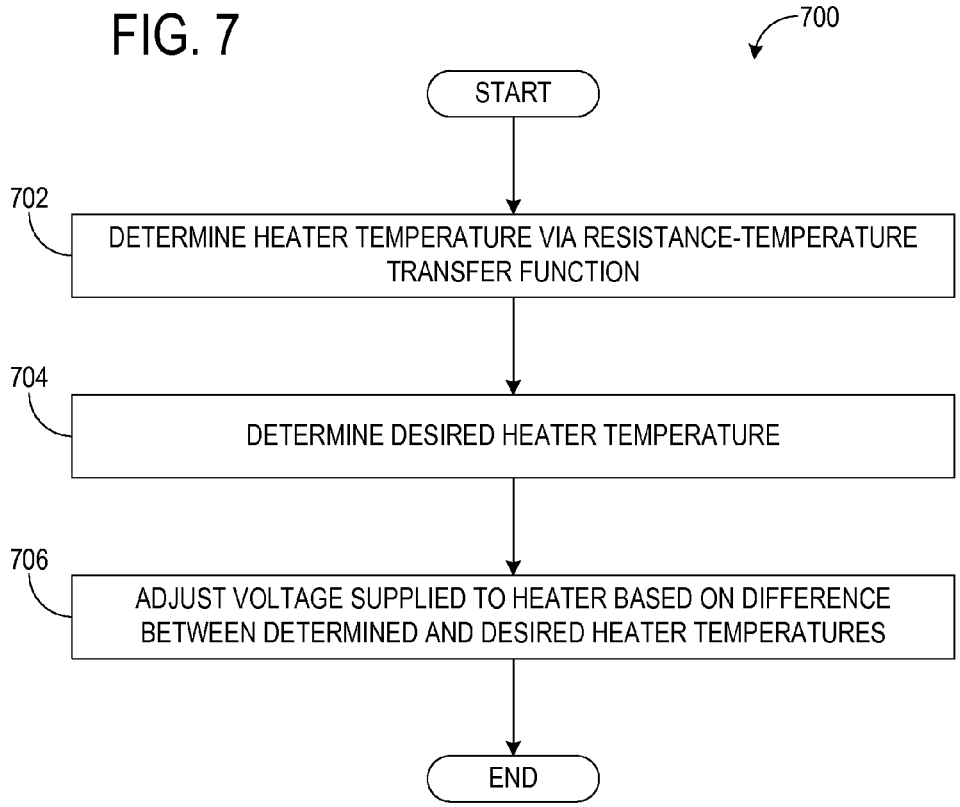
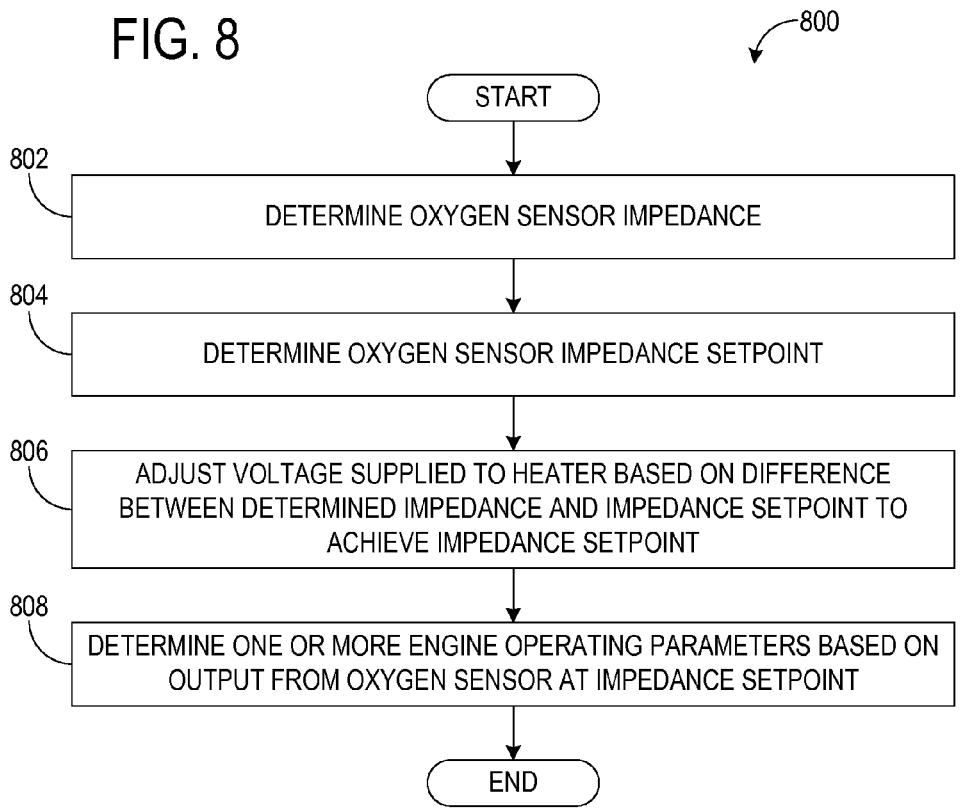

OXYGEN SENSOR CONTROL RESPONSIVE TO RESISTANCE AND IMPEDANCE

FIELD

The field of the disclosure relates generally to oxygen sensor control.

BACKGROUND AND SUMMARY

Intake and/or exhaust gas sensors may be operated to provide indications of various exhaust gas constituents. For example, an oxygen sensor positioned in an engine exhaust system may be used to determine the air-fuel ratio (AFR) of exhaust gas, while an oxygen sensor positioned in an engine intake system may be used to determine the concentration of exhaust gas recirculation (EGR) gasses in intake charge air. Both parameters, among others that may be measured via an oxygen sensor, may be used to adjust various aspects of engine operation. An engine may be controlled to achieve a desired exhaust gas AFR based on the AFR indicated by an oxygen sensor to maximize operating efficiency of an emission control device, for example. For some oxygen sensors, their output may significantly vary as a function of their operating temperature. Accordingly, such oxygen sensors may be heated by a heating element to bring the sensor temperature within a desired range such that desired oxygen sensing is provided. In some examples, the heating element is controlled according to a desired temperature and an inferred temperature, which may be determined based on the resistance of the heating element, as the heater resistance may vary linearly with heater temperature. The resistance-temperature heater transfer function may differ among different oxygen sensors, however.

U.S. Pat. App. No. 2003/0019865 discloses methods of controlling a heating element of an exhaust gas oxygen sensor. Particularly, disparities in the resistance-temperature heater transfer function among oxygen sensors due to sensor-to-sensor variability are recognized and addressed by employing an adaptive offset (e.g., forming, with other parameters, a y-intercept) in a linear function relating heating element temperature to heating element resistance. The offset is adjusted based on a deviation between a measured heating element resistance from its nominal value under predetermined conditions at engine start-up. The linear function includes a slope relating heater resistance to heater temperature that is manufacturer-specified.

The inventors herein have recognized an issue with the approach identified above. Variance in the resistance-temperature transfer function of an oxygen sensor may include variance in both the offset and slope of a linear function used to determine heating element temperature as a function of heating element resistance. Being manufacturer-specified, the slope of the above-identified approach is not adapted throughout the life of an oxygen sensor, which may lead to inaccurate oxygen sensor control that can in turn cause increased emissions, decreased fuel economy, and decreased vehicle drivability.

Oxygen sensors may exhibit additional variability that can affect sensor and heating element control. In some approaches, the temperature of an oxygen sensor is controlled based on the impedance of a sensor element (e.g., a Nernst concentration cell) of the sensor; as the sensor element impedance may be a function of temperature, the sensor temperature may be controlled to a desired temperature by bringing the sensor element impedance to a desired impedance. The relation between sensor element impedance and temperature often varies among oxygen sensors, however, and with age.

U.S. Pat. No. 5,852,228 discloses methods and apparatuses for achieving a target sensor element impedance so as to bring an oxygen sensor to a desired temperature. The increase of sensor element impedance with sensor element deterioration is recognized and addressed by altering the target impedance as a function of the power supplied to the sensor heating element. Specifically, one of four target impedances may be selected depending on the average power supplied to the heating element. A transition from a relatively lower target impedance to a relatively higher target impedance may be achieved by incrementing the relatively lower impedance by a predetermined amount.

The inventors herein have recognized an issue with such an approach. In some scenarios, controlling an oxygen sensor based on a target impedance selected from four target impedances may result in an undesired sensor temperature that fails to enable desired sensor operation and/or can potentially degrade sensor operation, due to the lack of granularity of the selectable impedances. This issue is exacerbated by sensor aging, which may cause variation in the relation between impedance and temperature in the sensor.

One approach that addresses at least some of the above-identified issues includes a method of operating an oxygen sensor including a heater comprising sampling a first heater resistance at a first temperature, and determining a resistance-temperature transfer function relating heater resistance to heater temperature based on the first heater resistance and a second heater resistance at a second temperature, the second temperature different from the first temperature.

Another approach that addresses at least some of the above-identified issues includes a method of controlling an oxygen sensor comprising, responsive to determining that a temperature of the oxygen sensor corresponds to a desired temperature, determining an impedance of the oxygen sensor, setting an impedance setpoint to the determined impedance, and controlling the oxygen sensor so that the impedance of the oxygen sensor corresponds to the impedance setpoint.

In this way, the temperature of an oxygen sensor may be accurately controlled throughout its operational life, enabling increased accuracy of output from the oxygen sensor and parameters derived therefrom. Thus, the technical result is achieved by these actions.

The above advantages and other advantages, and features of the present description will be readily apparent from the following Detailed Description when taken alone or in connection with the accompanying drawings.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure. Finally, the above explanation does not admit any of the information or problems were well known.

BRIEF DESCRIPTION OF THE DRAWINGS

FIG. 7 shows a flowchart illustrating a method of controlling the voltage supplied to an oxygen sensor heater.

FIG. 8 shows a flowchart illustrating a method of determining one or more engine operating parameters based on output from an oxygen sensor.

DETAILED DESCRIPTION

Figure 1:
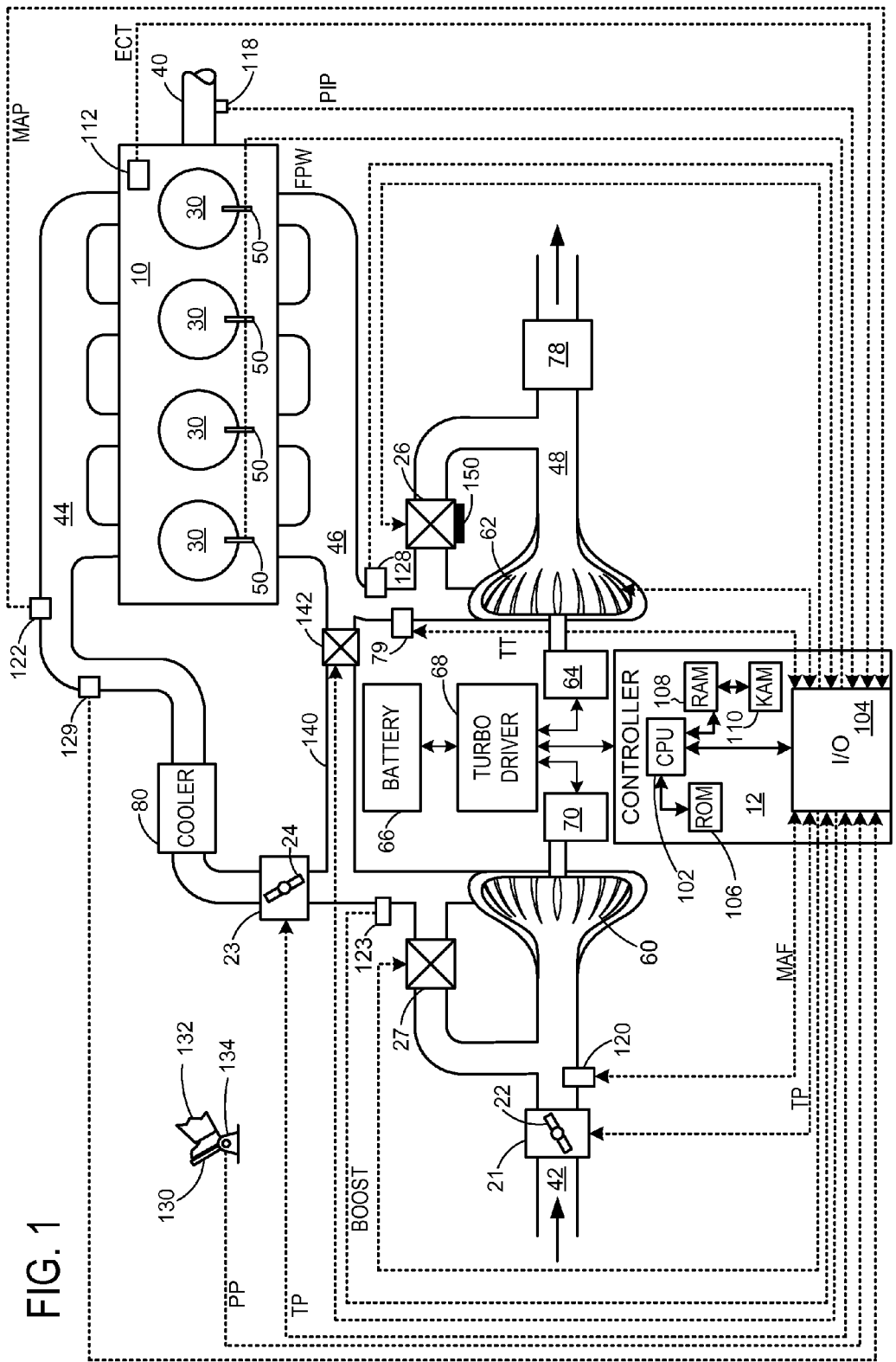
FIG. 1 is a schematic diagram showing an example engine.
Figure 2:
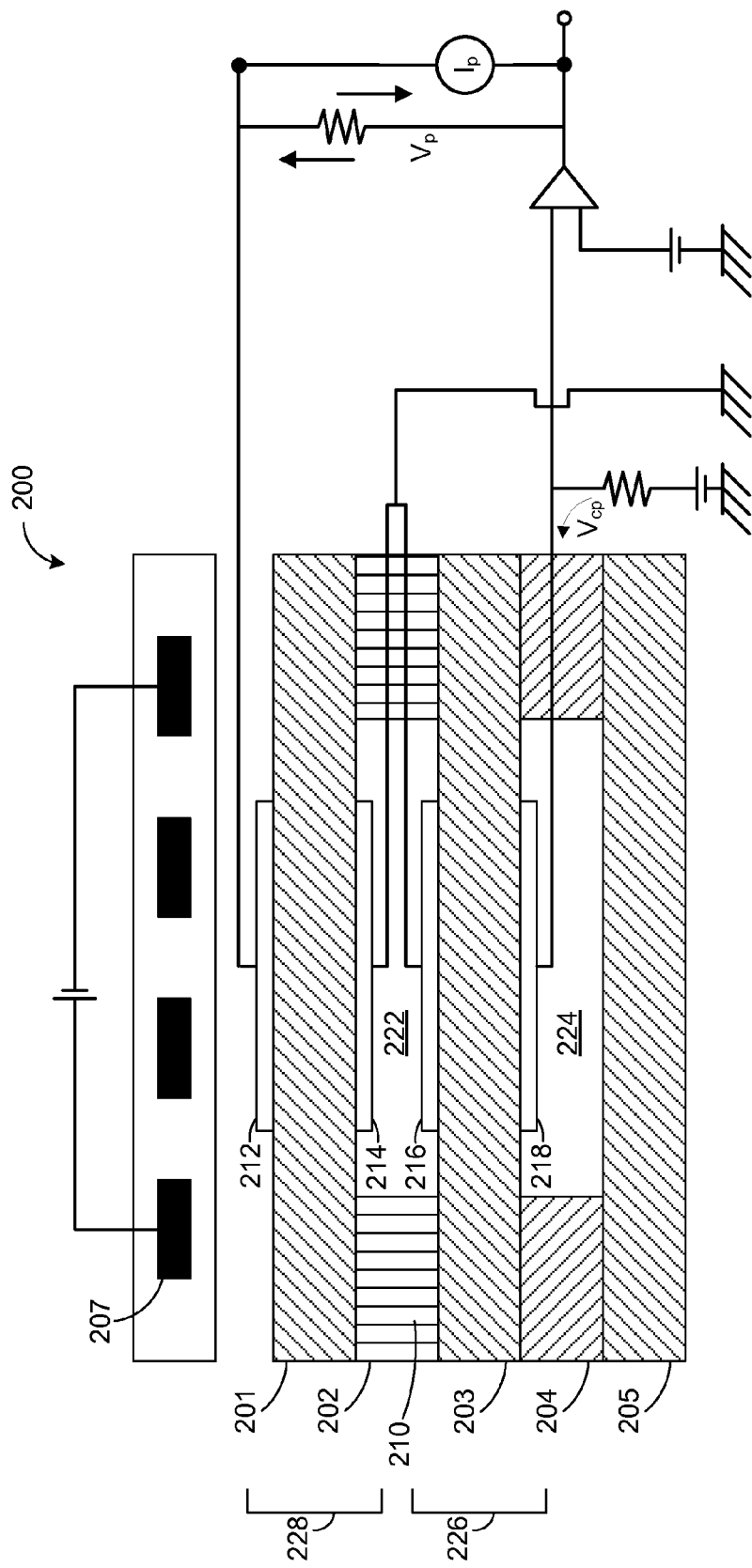
FIG. 2 shows a schematic view of an example oxygen sensor.
Figure 3:
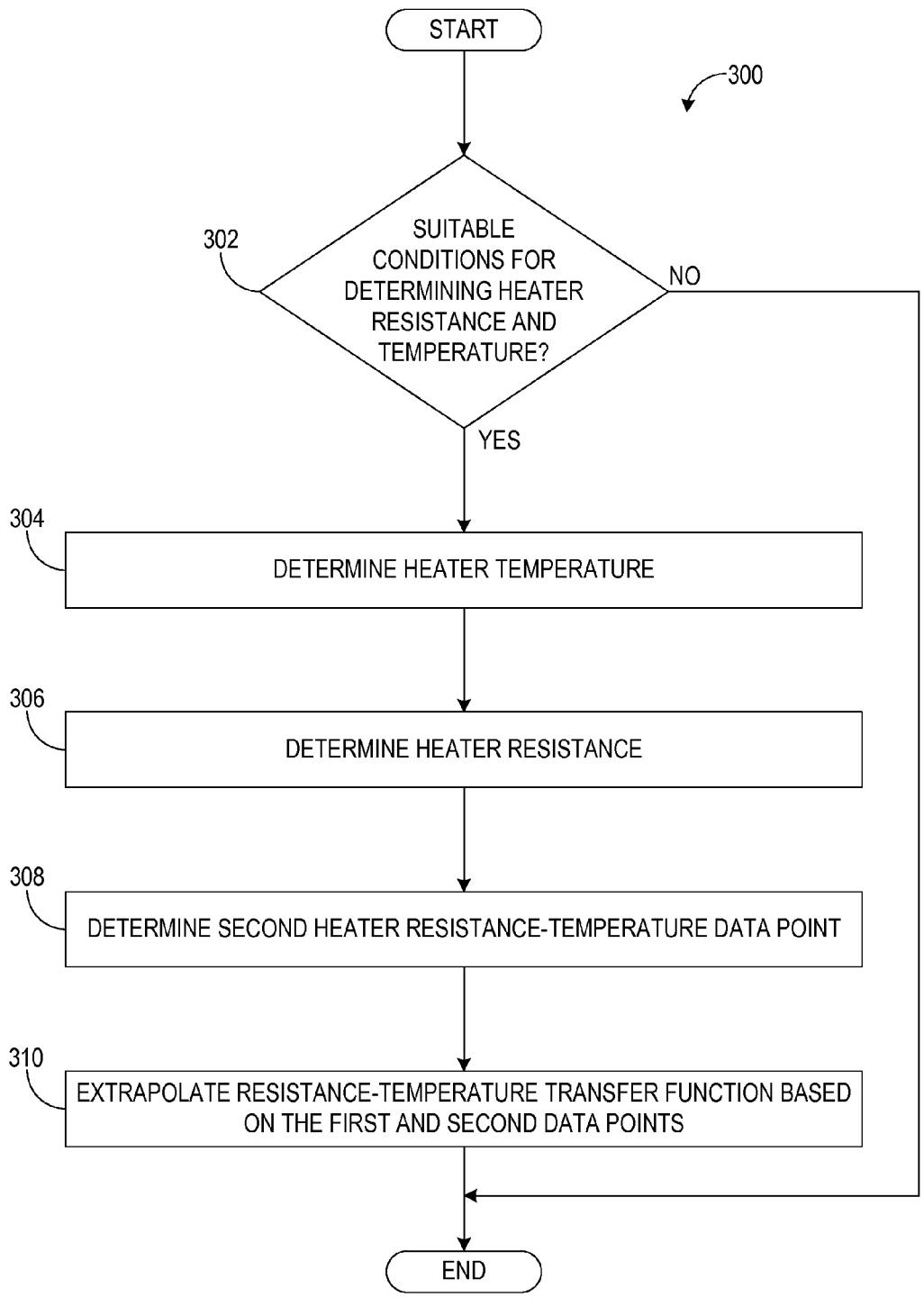
FIG. 3 shows a flowchart illustrating a method of determining a resistance-temperature transfer function for an oxygen sensor heater.
Figure 4:
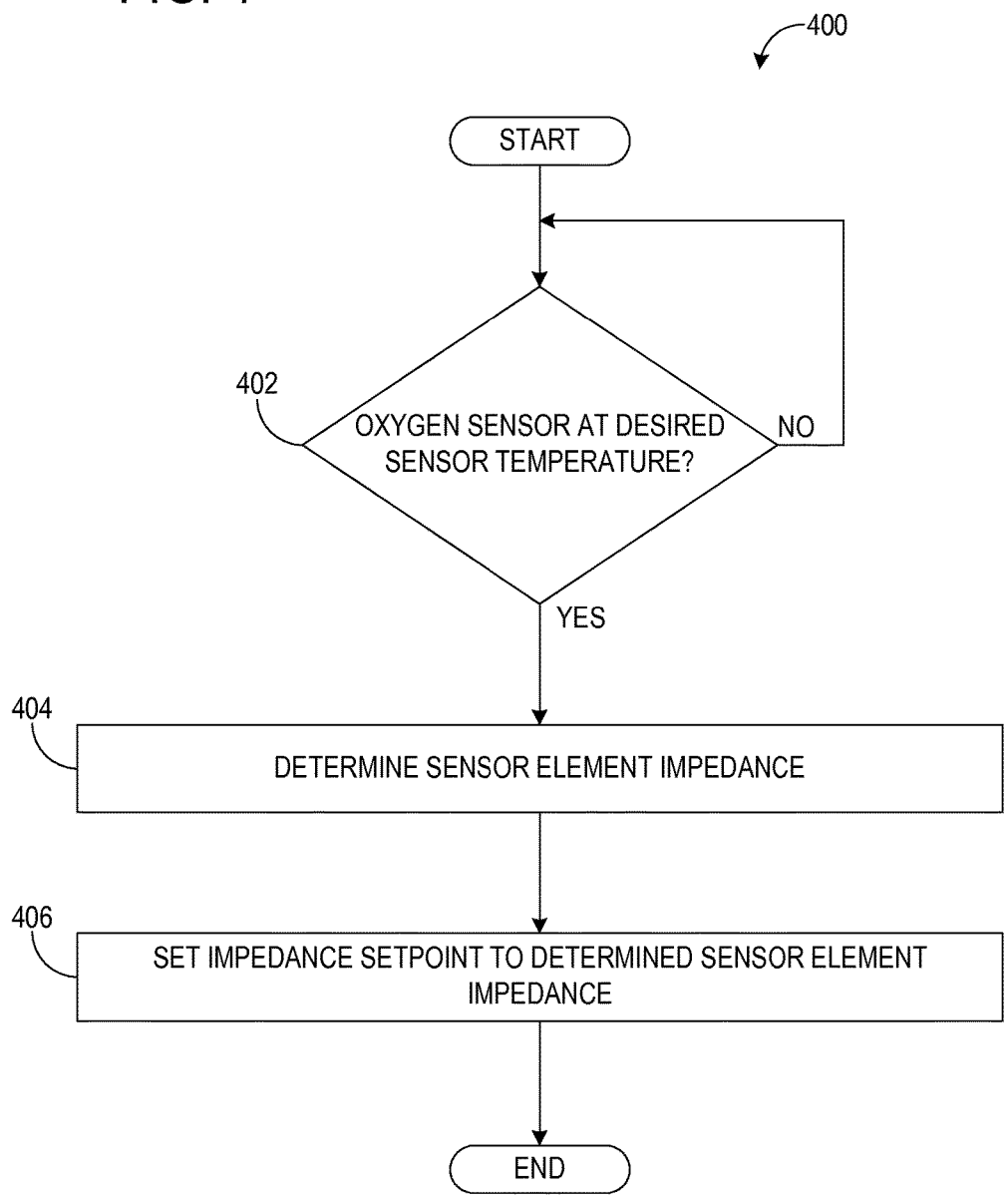
FIG. 4 shows a flowchart illustrating a method of determining an impedance setpoint of an oxygen sensor.
Figure 5:
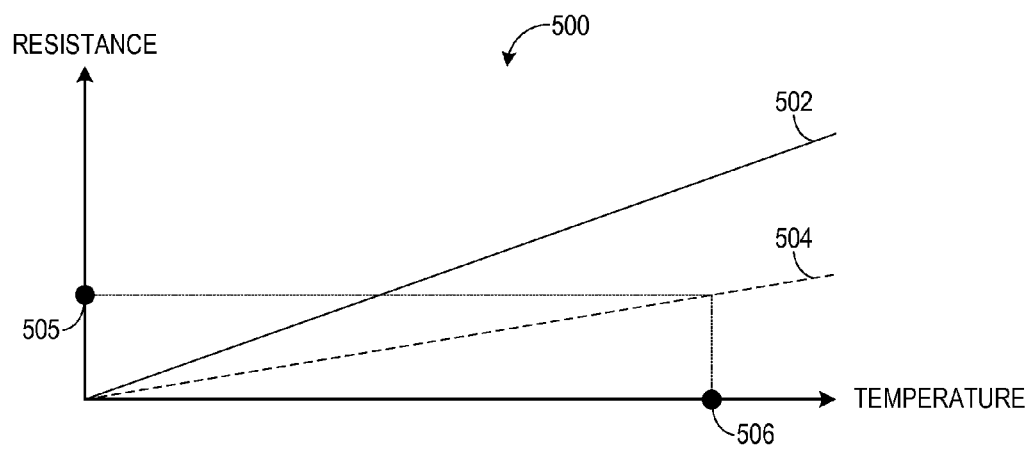
FIG. 5 shows a plot illustrating determination of a resistance-temperature transfer function for an oxygen sensor heater.
Figure 6:
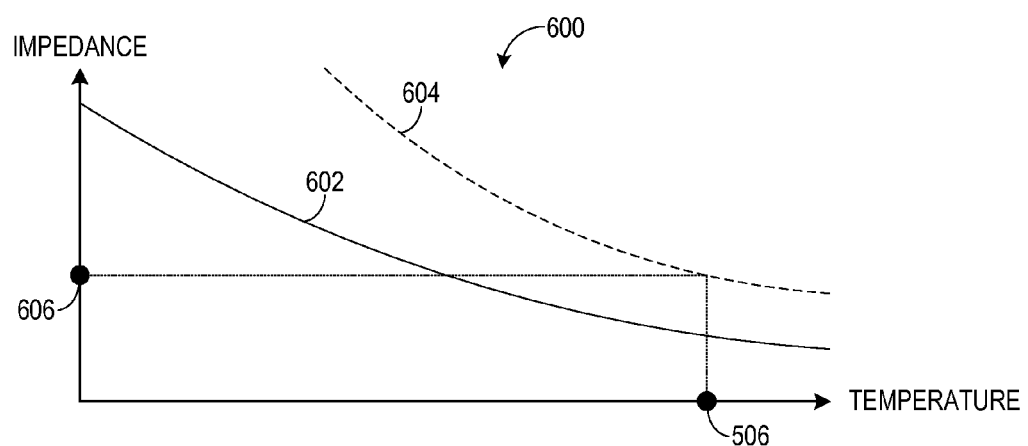
FIG. 6 shows a plot illustrating determination of an impedance setpoint for an oxygen sensor.

Various methods are provided for operating an oxygen sensor. In one example, a method of operating an oxygen sensor including a heater comprises sampling a first heater resistance at a first temperature, and determining a resistance-temperature transfer function relating heater resistance to heater temperature based on the first heater resistance and a second heater resistance at a second temperature, the second temperature different from the first temperature. FIG. 1 is a schematic diagram showing an example engine, FIG. 2 shows a schematic view of an example oxygen sensor, FIG. 3 shows a flowchart illustrating a method of determining a resistance-temperature transfer function for an oxygen sensor heater, FIG. 4 shows a flowchart illustrating a method of determining an impedance setpoint of an oxygen sensor, FIG. 5 shows a plot illustrating determination of a resistance-temperature transfer function for an oxygen sensor heater, FIG. 6 shows a plot illustrating determination of an impedance setpoint for an oxygen sensor, FIG. 7 shows a flowchart illustrating a method of controlling the voltage supplied to an oxygen sensor heater, and FIG. 8 shows a flowchart illustrating a method of determining one or more engine operating parameters based on output from an oxygen sensor. The engine of FIG. 1 also includes a controller configured to carry out the methods depicted in FIGS. 3, 4, 7, and 8.

FIG. 1 is a schematic diagram showing an example engine 10, which may be included in a propulsion system of an automobile. The engine 10 is shown with four cylinders 30. However, other numbers of cylinders may be used in accordance with the current disclosure. Engine 10 may be controlled at least partially by a control system including controller 12, and by input from a vehicle operator 132 via an input device 130. In this example, input device 130 includes an accelerator pedal and a pedal position sensor 134 for generating a proportional pedal position signal PP. Each combustion chamber (e.g., cylinder) 30 of engine 10 may include combustion chamber walls with a piston (not shown) positioned therein. The pistons may be coupled to a crankshaft 40 so that reciprocating motion of the piston is translated into rotational motion of the crankshaft. Crankshaft 40 may be coupled to at least one drive wheel of a vehicle via an intermediate transmission system (not shown). Further, a starter motor may be coupled to crankshaft 40 via a flywheel to enable a starting operation of engine 10.

Combustion chambers 30 may receive intake air from intake manifold 44 via intake passage 42 and may exhaust combustion gasses via exhaust passage 48. Intake manifold 44 and exhaust manifold 46 can selectively communicate with combustion chamber 30 via respective intake valves and exhaust valves (not shown). In some embodiments, combustion chamber 30 may include two or more intake valves and/or two or more exhaust valves.

Fuel injectors 50 are shown coupled directly to combustion chamber 30 for injecting fuel directly therein in proportion to the pulse width of signal FPW received from controller 12. In this manner, fuel injector 50 provides what is known as direct injection of fuel into combustion chamber 30. The fuel injector may be mounted in the side of the combustion chamber or in the top of the combustion chamber, for example. Fuel may be delivered to fuel injector 50 by a fuel system (not shown) including a fuel tank, a fuel pump, and a fuel rail. In some embodiments, combustion chambers 30 may alternatively, or additionally, include a fuel injector arranged in intake manifold 44 in a configuration that provides what is known as port injection of fuel into the intake port upstream from each combustion chamber 30.

Intake passage 42 may include throttle 21 and 23 having throttle plates 22 and 24, respectively. In this particular example, the position of throttle plates 22 and 24 may be varied by controller 12 via signals provided to an actuator included with throttles 21 and 23. In one example, the actuators may be electric actuators (e.g., electric motors), a configuration that is commonly referred to as electronic throttle control (ETC). In this manner, throttles 21 and 23 may be operated to vary the intake air provided to combustion chamber 30 among other engine cylinders. The position of throttle plates 22 and 24 may be provided to controller 12 by throttle position signal TP. Intake passage 42 may further include a mass air flow sensor 120, a manifold air pressure sensor 122, and a throttle inlet pressure sensor 123 for providing respective signals MAF (mass airflow) MAP (manifold air pressure) to controller 12.

Exhaust passage 48 may receive exhaust gasses from cylinders 30. Exhaust gas sensor 128 is shown coupled to exhaust passage 48 upstream of turbine 62 and emission control device 78. Sensor 128 may be selected from among various suitable sensors for providing an indication of exhaust gas air/fuel ratio such as a linear oxygen sensor or UEGO (universal or wide-range exhaust gas oxygen), a two-state oxygen sensor or EGO, a NOx, HC, or CO sensor, for example. Emission control device 78 may be a three way catalyst (TWC), NOx trap, various other emission control devices, or combinations thereof.

FIG. 1 also illustrates the inclusion of an intake air sensor 129 coupled to intake passage 42. Sensor 129 may be any suitable sensor for providing an indication of intake air oxygen content such as a linear oxygen sensor or UEGO (universal or wide-range exhaust gas oxygen), a two-state oxygen sensor or EGO, a HEGO (heated EGO), a $NO_x$, HC, or CO sensor, for example. In some implementations, both sensor 128 and sensor 129 may be included in engine 10 as shown in FIG. 1, while in other implementations one and not the other of sensors 128 and 129 may be included.

Exhaust temperature may be measured by one or more temperature sensors (not shown) located in exhaust passage 48. Alternatively, exhaust temperature may be inferred based on engine operating conditions such as speed, load, AFR, spark retard, etc.

Controller 12 is shown in FIG. 1 as a microcomputer, including microprocessor unit 102, input/output ports 104, an electronic storage medium for executable programs and calibration values shown as read only memory chip 106 in this particular example, random access memory 108, keep alive memory 110, and a data bus. Controller 12 may receive various signals from sensors coupled to engine 10, in addition to those signals previously discussed, including measurement of inducted mass air flow (MAF) from mass air flow sensor 120; engine coolant temperature (ECT) from temperature sensor 112, shown schematically in one location within the engine 10; a profile ignition pickup signal (PIP) from Hall effect sensor 118 (or other type) coupled to crankshaft 40; the throttle position (TP) from a throttle position sensor, as discussed; and absolute manifold pressure signal, MAP, from sensor 122, as discussed. Engine speed signal, RPM, may be generated by controller 12 from signal PIP. Manifold pressure signal MAP from a manifold pressure sensor may be used to provide an indication of vacuum, or pressure, in the intake manifold 44. Note that various combinations of the above sensors may be used, such as a MAF sensor without a MAP sensor, or vice versa. During stoichiometric operation, the MAP sensor can give an indication of engine torque. Further, this sensor, along with the detected engine speed, can provide an estimate of charge (including air) inducted into the cylinder. In one example, sensor 118, which is also used as an engine speed sensor, may produce a predetermined number of equally spaced pulses every revolution of the crankshaft 40. In some examples, storage medium read-only memory 106 may be programmed with computer readable data representing instructions executable by processor 102 for performing the methods described below as well as other variants that are anticipated but not specifically listed.

Engine 10 may further include a compression device such as a turbocharger or supercharger including at least a compressor 60 arranged along intake manifold 44. For a turbocharger, compressor 60 may be at least partially driven by a turbine 62, via, for example a shaft, or other coupling arrangement. The turbine 62 may be arranged along exhaust passage 48 and communicate with exhaust gasses flowing therethrough. Various arrangements may be provided to drive the compressor. For a supercharger, compressor 60 may be at least partially driven by the engine and/or an electric machine, and may not include a turbine. Thus, the amount of compression provided to one or more cylinders of the engine via a turbocharger or supercharger may be varied by controller 12. In some cases, the turbine 62 may drive, for example, an electric generator 64, to provide power to a battery 66 via a turbo driver 68. Power from the battery 66 may then be used to drive the compressor 60 via a motor 70. Further, a sensor 123 may be disposed in intake manifold 44 for providing a BOOST signal to controller 12.

Further, exhaust passage 48 may include wastegate 26 for diverting exhaust gas away from turbine 62. In some embodiments, wastegate 26 may be a multi-staged wastegate, such as a two-staged wastegate with a first stage configured to control boost pressure and a second stage configured to increase heat flux to emission control device 78. Wastegate 26 may be operated with an actuator 150, which may be an electric actuator such as an electric motor, for example, though pneumatic actuators are also contemplated. Intake passage 42 may include a compressor bypass valve 27 configured to divert intake air around compressor 60. Wastegate 26 and/or compressor bypass valve 27 may be controlled by controller 12 via actuators (e.g., actuator 150) to be opened when a lower boost pressure is desired, for example.

Intake passage 42 may further include charge air cooler (CAC) 80 (e.g., an intercooler) to decrease the temperature of the turbocharged or supercharged intake gasses. In some embodiments, charge air cooler 80 may be an air to air heat exchanger. In other embodiments, charge air cooler 80 may be an air to liquid heat exchanger.

Further, in the disclosed embodiments, an exhaust gas recirculation (EGR) system may route a desired portion of exhaust gas from exhaust passage 48 to intake passage 42 via EGR passage 140. The amount of EGR provided to intake passage 42 may be varied by controller 12 via EGR valve 142. Further, an EGR sensor (not shown) may be arranged within the EGR passage and may provide an indication of one or more of pressure, temperature, and concentration of the exhaust gas. Alternatively, the EGR may be controlled through a calculated value based on signals from the MAF sensor (upstream), MAP (intake manifold), MAT (manifold gas temperature) and the crank speed sensor. Further, the EGR may be controlled based on an exhaust $O_2$ sensor and/or an intake oxygen sensor (intake manifold).

For example, the EGR dilution percentage of the intake charge at a given time (e.g., the proportion of combusted gases to air in an intake passage of the engine) may be inferred from the output of the intake air sensor 129 (e.g., intake oxygen sensor). In particular, when oxygen intake concentration is reduced, an increase in EGR may be inferred since the presence of EGR may dilute oxygen in the intake stream at the intake air sensor 129. Conversely, when oxygen intake concentration increases, a decrease in EGR may be inferred due to a reduction of EGR. Controller 12 may estimate the percent dilution of the EGR flow based on feedback from intake air sensor 129. Further, the controller 12 may then estimate an EGR amount or EGR flow rate based on feedback from the intake air sensor 129. In some examples, the controller 12 may then adjust one or more of the EGR valve 142, throttle 23, compressor bypass valve 27, and wastegate 26 to achieve a desired EGR dilution percentage of the intake charge and/or desired EGR flow rate.

Under some conditions, the EGR system may be used to regulate the temperature of the air and fuel mixture within the combustion chamber. FIG. 1 shows a high pressure EGR system where EGR is routed from upstream of a turbine of a turbocharger to downstream of a compressor of a turbocharger. In other embodiments, the engine may additionally or alternatively include a low pressure EGR system where EGR is routed from downstream of a turbine of a turbocharger to upstream of a compressor of the turbocharger.

FIG. 2 shows a schematic view of an example embodiment of an oxygen sensor 200 configured to measure one or more constituents of a gas stream (e.g., oxygen concentration in an intake airflow or in an exhaust stream). In some examples, the sensor 200 may be a UEGO sensor. The sensor 200 may thus correspond to one or both of sensors 128 and 129 of FIG. 1, for example. It will be appreciated, however, that sensors 128 and 129 may deviate in some respects from the sensor 200—for example, they may employ one or more modifications.

As shown in FIG. 2, the sensor 200 comprises a plurality of layers of one or more ceramic materials arranged in a stacked configuration. In the embodiment of FIG. 2, five ceramic layers are depicted as layers 201, 202, 203, 204, and 205. These layers include one or more layers of a solid electrolyte capable of conducting ionic oxygen. Examples of suitable solid electrolytes include, but are not limited to, zirconium oxide-based materials. Further, in some embodiments, a heater 207 may be disposed in thermal communication with the layers to increase the ionic conductivity of the layers. While the depicted oxygen sensor is formed from five ceramic layers, it will be appreciated that the oxygen sensor may include other suitable numbers of ceramic layers.

The layer 202 includes a material or materials creating a diffusion path 210. The diffusion path 210 is configured to introduce gasses into a first internal cavity 222 via diffusion. The diffusion path 210 may be configured to allow one or more components of intake air or exhaust gasses, including but not limited to a desired analyte (e.g., $O_2$), to diffuse into internal cavity 222 at a more limiting rate than the analyte can be pumped in or out by a pumping electrodes pair 212 and 214. In this manner, a stoichiometric level of $O_2$ may be obtained in the first internal cavity 222.

The sensor 200 further includes a second internal cavity 224 within the layer 204 separated from the first internal cavity 222 by the layer 203. The second internal cavity 224 is configured to maintain a constant oxygen partial pressure equivalent to a stoichiometric condition; e.g., an oxygen level present in the second internal cavity 224 is equal to that which the intake air or exhaust gas would have if the air-fuel ratio were stoichiometric. The oxygen concentration in the second internal cavity 224 is held constant by pumping voltage $V_{cp}$. Herein, the second internal cavity 224 may be referred to as a reference cell.

A pair of sensing electrodes 216 and 218 is disposed in communication with the first internal cavity 222 and the reference cell 224. The sensing electrodes pair 216 and 218 detects a concentration gradient that may develop between the first internal cavity 222 and the reference cell 224 due to an oxygen concentration in the intake air or exhaust gas that is higher than or lower than the stoichiometric level. A high oxygen concentration may be caused by a lean intake air or exhaust gas mixture, while a low oxygen concentration may be caused by a rich mixture.

The pair of pumping electrodes 212 and 214 is disposed in communication with the internal cavity 222, and is configured to electrochemically pump a selected gas constituent (e.g., $O_2$) from internal cavity 222 through layer 201 and out of the sensor 200. Alternatively, the pair of pumping electrodes 212 and 214 may be configured to electrochemically pump a selected gas through layer 201 and into internal cavity 222. Herein, the pumping electrodes pair 212 and 214 may be referred to as an $O_2$ pumping cell.

The electrodes 212, 214, 216, and 218 may be made of various suitable materials. In some embodiments, the electrodes 212, 214, 216, and 218 may be at least partially made of a material that catalyzes the dissociation of molecular oxygen. Examples of such materials include, but are not limited to, electrodes containing platinum and/or silver.

The process of electrochemically pumping the oxygen out of or into the internal cavity 222 includes applying a voltage $V_p$ across the pumping electrode pair 212 and 214. The pumping voltage $V_p$ applied to the $O_2$ pumping cell pumps oxygen into or out of the first internal cavity 222 in order to maintain a stoichiometric level of oxygen in the cavity pumping cell. The resulting pumping current $I_p$ is proportional to the concentration of oxygen in the exhaust gas. A suitable control system (not shown in FIG. 2) generates the pumping current signal $I_p$ as a function of the intensity of the applied pumping voltage $V_p$ required to maintain a stoichiometric level within the first internal cavity 222. Thus, a lean mixture will cause oxygen to be pumped out of the internal cavity 222 and a rich mixture will cause oxygen to be pumped into the internal cavity 222.

It should be appreciated that oxygen sensor 200 is merely an example embodiment of an oxygen sensor, and that other embodiments of oxygen sensors may have additional and/or alternative features and/or designs without departing from the scope of this disclosure.

Because the output of oxygen sensor 200 may vary significantly with temperature, accurate control of the oxygen sensor temperature may be desired. For example, oxygen sensor 200 may provide desired sensing above a lower threshold temperature (e.g., a light-off temperature between 720° C. and 830° C.); as such, the oxygen sensor temperature may be raised above the lower threshold under conditions in which the sensor temperature is below the lower threshold (e.g., at engine cold start). On the other hand, excessive temperatures may degrade operation of oxygen sensor 200, and as such, the sensor temperature may be maintained below an upper threshold.

In some examples, the resistance of heater 207 may be used to determine the temperature of the heater, enabling accurate control of the heater temperature and temperature of oxygen sensor 200. Heater 207 may be comprised of one or more materials (e.g., platinum), where the combined resistance of the one or more materials is directly proportional (e.g., linearly) to its temperature. Since the temperature of heater 207 correlates to the temperature of oxygen sensor 200 (e.g., due to physical proximity therebetween), the heater temperature may be used to assess temperature of the overall oxygen sensor as described in further detail below.

Part-to-part variability and aging may alter the relation between the resistance of heater 207 and the temperature of the heater. In particular, the resistance of heater 207 may be a function of its length and cross sectional area, both of which vary among oxygen sensors and as a function of time. Thus, a resistance-temperature transfer function determined for heater 207 may become unacceptably inaccurate over time, and may be unacceptably inaccurate when applied to a different heater which may or may have not undergone significant aging. As a non-limiting example illustrating such variation in the resistance-temperature transfer function, for a first oxygen sensor the resistance of its heater may be 4Ω at 20° C., while for a second oxygen sensor the resistance of its heater may be 4Ω at 600° C.

Accordingly, approaches are described herein for compensating variation in the resistance-temperature transfer function of an oxygen sensor heater. In some embodiments, variation in the resistance-temperature transfer function of heater 207 may be compensated by sampling the resistance of the heater at a known temperature and utilizing predetermined knowledge of the material composition of the heater. In particular, the materials comprising heater 207 may exhibit a known, fixed resistance at a given temperature. Thus, heater 207, when comprised of such materials, may exhibit this fixed resistance at the given temperature irrespective of its physical configuration, part-to-part variability, and aging. For example, heater 207 may be comprised of a particular composition of platinum (e.g., pure platinum with very few grain boundaries) that exhibits a known resistance of 0Ω at absolute zero (e.g., 0 K, −273.15° C.). More specifically, the resistivity of such a platinum composition falls to 0 Ω·m at absolute zero; consequently, the resistance (which may be a function of the product of resistivity with the ratio of length to cross sectional area) at absolute zero will be 0Ω, and variation in the length and/or cross sectional area will not cause this resistance to deviate from 0Ω at absolute zero. Other material compositions having one or more materials including platinum may be employed, however, in which case the material composition may exhibit a resistance of approximately 0Ω (e.g., between 0 and 10Ω) at absolute zero.

As described above, the resistance of heater 207 may vary linearly with temperature. In such a case, an updated resistance-temperature transfer function may be determined for heater 207 based on two data points: the known, fixed resistance at the given temperature (e.g., 0Ω at absolute zero for above-described platinum composition), which yields the y-intercept of the transfer function, and a sampled resistance at a known temperature. The transfer function may then be extrapolated from these two data points for a range of temperatures (e.g., the range of temperatures that may be assumed by oxygen sensor 200 throughout operation). It will be appreciated that the above-described platinum composition is provided as a non-limiting example, and that a known (e.g., predetermined) resistance at a given temperature may be used (in combination with a sampled resistance at a known temperature) to determine an updated resistance-temperature transfer function for heater 207 for a material composition that may be employed by the heater (e.g., a combination of platinum and aluminum oxide, a combination of platinum, palladium, and aluminum oxide).

In some examples, the resistance of heater 207, which may comprise a second data point used to determine an updated resistance-temperature transfer function of the heater, may be sampled upon vehicle key-on if an associated engine (e.g., engine 10 of FIG. 1) has been shut off for at least a threshold duration. The threshold duration may assume various suitable values and may correspond to a duration upon whose expiration the engine and oxygen sensor 200 have both cooled to ambient temperatures (e.g., 20° C.). Here, since the engine and oxygen sensor 200 may both reside at approximately the same temperature, temperature may be measured at a variety of locations in the engine and/or vehicle. Referring to FIG. 1, temperature sensor 112 may be used to assess the temperature of oxygen sensor 200 in the event of key-on and expiration of the threshold duration. Other sensors such as an ambient temperature sensor may be used, however. Measurement of the temperature and resistance of heater 207 may be performed substantially concurrently and stored in a suitable data structure (e.g., lookup table). With the y-intercept of the linear resistance-temperature transfer function known via the predetermined knowledge of the heater material composition, the slope may be determined according to its mathematical definition—e.g., by computing the ratio of the difference between the two resistance values to the difference between the two temperature values. For embodiments in which heater 207 is comprised of a particular composition of platinum, the slope may be determined as the ratio of the sampled resistance (e.g., the non-zero resistance sampled upon key-on and expiration of the threshold duration) to the corresponding inferred heater temperature (e.g., an engine/vehicle temperature as measured by temperature sensor 112 of FIG. 1, an ambient temperature sensor).

In some implementations, sampling of the heater resistance and temperature may be performed at each vehicle key-on if the engine has been shut off for at least the threshold duration as described above. In this way, an accurate resistance-temperature transfer function may be maintained for heater 207 throughout its operational life. If, however, the engine has not been shut off for at least the threshold duration upon vehicle key-on, the heater resistance and temperature may not be sampled, and, alternatively, a previously sampled heater resistance and temperature may be used to determine the transfer function. The previously sampled heater resistance and temperature may be the most recently sampled resistance and temperature, for example. In some embodiments, two or more previously sampled heater resistances and temperatures may be averaged if the instant heater resistance and temperature cannot be sampled.

In some examples, determining the resistance-temperature transfer function of heater 207 may include sampling the heater resistance upon vehicle key-on and expiration of the threshold duration as described above, and further sampling the heater resistance once oxygen sensor 200 has reached its operational temperature (e.g., 830° C.). The resistance-temperature data point sampled once the operational temperature has been reached may have a known and acceptable error in temperature (e.g., +/−20° C.). However, this resistance-temperature data point sampled at the operational temperature may be used with the initially sampled resistance-temperature data point to extrapolate the resistance-temperature transfer function, as the error of the transfer function may be acceptably low due to extrapolating over a wide temperature range (e.g., 1100° C., or, from −273.15° C. to 830° C.). In some implementations, two or more resistance-temperature data points may be sampled once oxygen sensor 200 has reached the operational temperature. Such data points may be collected in a relatively short period of time relatively early in the operational life of oxygen sensor 200 and averaged so as to minimize error and avoid relatively greater error that may result from sampling data points later in the operational life of the sensor (e.g., due to aging).

By persistently updating the resistance-temperature transfer function of heater 207 in the manners described above, part-to-part variability and aging in the heater may be compensated and its temperature accurately determined throughout its operational life. Other types of variability (e.g., vehicle-to-vehicle, environmental, application-specific) may be compensated as well. Further, using the resistance of heater 207 to maintain an accurate resistance-temperature transfer function may enable the temperature of oxygen sensor 200 to be accurately determined throughout the entirety of its range of operational temperatures as described below. Consequently, the accuracy of parameters derived from output of oxygen sensor 200 may be increased—e.g., AFR and fuel-to-air ratio, which in turn may decrease emissions while increasing fuel economy and vehicle drivability. Increased accuracy in assessing the temperature of oxygen sensor 200 may also enable more accurate control of the reference voltage supplied to the oxygen sensor. Approaches that modulate this reference voltage to determine various parameters of interest (e.g., pumping current, ethanol content) may benefit from this increased accuracy. Increased accuracy in assessing the temperature of heater 207 may also extend the durability and operational life of oxygen sensor 200, as inaccurate heater control leading to thermal stress (which may cause flaking of an outer electrode of the sensor) may be avoided.

It will be appreciated that the approaches to updating a resistance-temperature transfer function of an oxygen sensor heater described above may be extended to configurations in which the relation between heater resistance and heater temperature is nonlinear. In this case, two or more data points (e.g., resistance-temperature coordinates) may be sampled under select conditions (e.g., upon key-on and expiration of the threshold duration, and/or the engine and/or vehicle being at substantially ambient temperatures) and combined with predetermined knowledge of the heater materials to sufficiently determine an updated transfer function. Various suitable curve-fitting techniques may be employed to determine the updated transfer function, for example.

Oxygen sensor 200 may provide desired sensing when brought to a range of operational temperatures (e.g., 720-830° C.). More specifically, one or both of a sensing cell 226, which comprises layer 203 and electrodes 216 and 218, and pumping cell 228, which comprises layer 201 and electrodes 212 and 214, may be brought to the range of operational temperatures to enable the desired sensing. The temperature of a cell may be controlled by adjusting the impedance of the cell, as cell temperature may be proportional to cell impedance.

It is well known that the conductivity of a material changes with temperature. For an oxygen ionic conducting electrolyte such as zirconia, the ionic conductivity typically increases as the temperature increases. Other factors such as impurities, grain boundaries, structure, and geometry can affect the conductivity of the zirconia. For a fixed geometry and structure, the impedance (which is the inverse of the conductivity) of a zirconia element is directly related (e.g., inversely proportional) to the temperature of the element. The oxygen sensor element impedance may be measured by measuring the voltage drop across the oxygen sensor element (e.g., by using an AC technique). For oxygen sensor 200, the sensor element impedance may be specifically measured across either sensing cell 226 or pumping cell 228. In this approach, impedance measurement of a cell may be based on the applied voltage and resulting current associated with that cell—e.g., the impedance of pumping cell 228 may be determined based on the pumping voltage $V_p$ applied to the pumping cell and the resulting pumping current $I_p$. The impedance of sensing cell 226 may be analogously determined based on the pumping voltage (e.g., $V_{cp}$) applied to the sensing cell and the resulting pumping current.

Accordingly, the temperature of oxygen sensor 200 may be controlled by controlling its impedance. For example, the impedance of a sensor element (e.g., pumping cell 228) may be measured in real time and used to control the temperature of oxygen sensor 200—e.g., the output of heater 207 may be controlled in closed loop fashion to minimize the difference between a desired sensor element impedance and an actual (e.g., measured) sensor element impedance. In this way, the difference between a desired sensor temperature and an actual sensor temperature may be minimized. The desired sensor temperature may thus be achieved by controlling the output of heater 207 according to the impedance of a sensor element of oxygen sensor 200.

In some implementations, a suitable data structure such as a lookup table may store one or more impedance setpoints and their resulting sensor temperatures such that the data structure may be accessed, by supplying a desired sensor temperature, to retrieve a corresponding impedance setpoint that, when applied to oxygen sensor 200, imbues the sensor with the desired senor temperature.

Part-to-part variability and aging in an oxygen sensor can alter the relation between sensor element impedance and temperature. As a non-limiting example, an impedance setpoint of 75Ω whose application is expected to result in a sensor temperature of 830° C. (e.g., an operational temperature) may actually result in a sensor temperature between 810° C. and 850° C. in a new (e.g., non-aged) oxygen sensor. Further alterations to the impedance-temperature relation may occur as the oxygen sensor ages—for example, second internal cavity 224 may undergo degradation as the sensor ages. Oxygen sensor 200 may exhibit increasingly greater temperatures as second internal cavity 224 degrades, when controlled according to the same impedance setpoint; for example, an aged oxygen sensor, when controlled according to an impedance setpoint of 75Ω, may exhibit a temperature of 950° C. when the application of the impedance setpoint was expected to result in a sensor temperature of 830° C. Usage of an impedance setpoint that results in an undesired sensor temperature may result in increased emissions, decreased fuel economy, and reduced vehicle drivability, for example.

Accordingly, approaches are described herein for compensating variation in an impedance setpoint and its corresponding sensor temperature. In some examples, an impedance setpoint, whose application to oxygen sensor 200 may no longer result in a desired sensor temperature, is updated upon determining that the sensor temperature corresponds to the desired sensor temperature. More specifically, the instant sensor element impedance (e.g., impedance of one or both of sensing cell 226 and pumping cell 228) is measured upon determining that the temperature of oxygen sensor 200 corresponds to the desired sensor temperature and selected as the updated impedance setpoint. The temperature of oxygen sensor 200 may be determined based on the temperature of heater 207, which in turn may be determined based on an up-to-date resistance-temperature transfer function for the heater as described herein. As a non-limiting example, an initial impedance setpoint of 75Ω is employed to achieve a desired oxygen sensor temperature of 830° C. The initial impedance setpoint may have been selected at the beginning of the operational life of the oxygen sensor, for example. Due to one or more factors such as aging, application of the impedance setpoint no longer results in the desired sensor temperature of 830° C., but instead 950° C. During operation of the oxygen sensor, and upon determining that the sensor has reached the desired sensor temperature of 830° C. (e.g., based on heater temperature), the instant sensor element impedance (e.g., 150Ω) is recorded and selected as the updated impedance setpoint. In the current state of the oxygen sensor, application of the updated impedance setpoint will now result in the desired sensor temperature.

As alluded to above, in some implementations the temperature of heater 207 may be used to assess the temperature of oxygen sensor 200. The temperature of heater 207 may be used to assess the temperature of oxygen sensor 200 due to their close physical proximity. A difference in the temperature of heater 207 and the temperature of oxygen sensor 200 may nevertheless exist due to their small separation—for example, slight heat loss may occur as oxygen sensor 200 is traversed from the heater to another region (e.g., one of sensing and pumping cells 226 and 228). As such, determining the temperature of oxygen sensor 200 based on the temperature of heater 207 may include applying an adjustment to the heater temperature to account for this difference. The adjustment may include a thermal gradient factor, for example, which may output a temperature adjustment for one or more inputs (e.g., three Cartesian inputs representing the difference between the three-dimensional position of heater 207 and the three-dimensional position of one or both of sensing cell 226 and pumping cell 228).

Thus, in the approach described above, an updated impedance setpoint may be determined for oxygen sensor 200 upon determining that the sensor temperature corresponds to a desired sensor temperature, where the sensor temperature is determined based on the resistance of heater 207. It will be appreciated, however, that other approaches may be used to determine whether the temperature of oxygen sensor 200 corresponds to the desired sensor temperature without departing from the scope of this disclosure.

The impedance setpoint of oxygen sensor 200 may be updated at various suitable frequencies. In some examples, the impedance setpoint may be updated to the measured instant sensor element impedance upon determining that the temperature of oxygen sensor 200 corresponds to a desired sensor temperature for each vehicle drive cycle.

It will be appreciated that determining the temperature of oxygen sensor 200 may include determining the temperature of one or more of its constituent elements. For example, the temperature of sensing cell 226 and/or the temperature of pumping cell 228 may be determined and considered as the temperature of the overall oxygen sensor 200. In this example, the thermal gradient factor may be employed to account for differences in thermal conditions between heater 207 and one or both of the sensing and pumping cells 226 and 228.

By maintaining an updated and accurate impedance setpoint whose application results in a desired oxygen sensor temperature, variance in the impedance-temperature relation (e.g., due to part-to-part variability, aging) of an oxygen sensor may be compensated. Consequently, output from the oxygen sensor, and parameters derived therefrom, may exhibit increased accuracy, which in turn may lead to reduced emissions, increased fuel economy, and increased vehicle drivability. Further, the operational life of the oxygen sensor may be extended by avoiding the application of impedance setpoints that would result in excessive sensor temperatures.

FIG. 3 shows a flowchart illustrating a method 300 of determining a resistance-temperature transfer function for an oxygen sensor heater. Method 300 may be employed to determine a resistance-temperature transfer function for heater 207 of oxygen sensor 200 (FIG. 2), for example. In some examples, method 300 may be employed to update an existing resistance-temperature transfer function, while in other examples, the method may be employed to derive a new resistance-temperature transfer function.

At 302 of method 300, it is determined whether operating conditions are suitable for determining the resistance and the temperature of an oxygen sensor heater. Assessing the operating conditions may include determining whether vehicle key-on has occurred. Assessing the operating conditions may further include determining whether, prior to vehicle key-on, an associated engine had been shut off (e.g., inactive) for at least a threshold duration. The threshold duration may correspond to a duration upon whose expiration the engine and the oxygen sensor have both cooled to substantially ambient temperatures (e.g., between 10° C. and 30° C.). If it is determined that vehicle key-on has occurred, and that the engine had been shut off for at least the threshold duration (YES), method 300 proceeds to 304. If both of these conditions are not met (NO), method 300 ends. In this case, a previously determined resistance-temperature transfer function of the oxygen sensor heater may be employed to perform the heater and sensor control described herein.

At 304 of method 300, the temperature of the heater is determined. In some examples, the heater temperature may be determined using a temperature sensor positioned at various locations in the engine or vehicle, as, due to expiration of the threshold duration, the engine and oxygen sensor reside at approximately the same temperature. The heater temperature may be measured with an ambient temperature sensor, for example. In other implementations, the heater temperature may be inferred in other manners. The heater temperature determined at 304 may be a first temperature such as an ambient temperature—e.g., a temperature between 10° C. and 30° C.

At 306 of method 300, the resistance of the heater is determined. Determination of the heater resistance may include applying a predetermined voltage to the heater and measuring the resultant current, and computing the resistance based on the voltage and current (e.g., via Ohm's law for when the heater is operating under Ohmic conditions).

The heater temperature determined at 304 and the heater resistance determined at 306 together may comprise a first data point used to determine the resistance-temperature transfer function of the heater.

At 308 of method 300, a second resistance-temperature data point of the heater is determined. In some examples, the second data point may include a resistance exhibited by the materials from which the heater is comprised at a given temperature; this resistance may be exhibited by the overall heater at the given temperature regardless of its physical configuration. In some examples, the second data point may be a known, fixed resistance for the materials—e.g., $0\Omega$ at 0 K for embodiments in which the heater is comprised of a particular composition of platinum (e.g., pure platinum having very few grain boundaries). In this example, determining the second data point may include retrieving the second data point from memory as it is already known. This second data point may thus comprise a second heater temperature different from the first heater temperature, and may be paired with a predetermined heater resistance. In other examples, however, the second resistance may be sampled (e.g., at an operational temperature of an oxygen sensor as described below).

At 310 of method 300, the resistance-temperature transfer function of the heater is extrapolated based on the first and second data points. In some examples, the resistance-temperature transfer function is linear, and as such, may be determined by computing the slope of the transfer function based on the first and second data points. The y-intercept may be given by the second data point. For scenarios in which the resistance-temperature transfer function is non-linear, however, the transfer function may be extrapolated from the first and second data points, and potentially additional data points which may be sampled as described herein, using various suitable curve-fitting techniques. Extrapolation may thus include extrapolating heater resistance for heater temperatures not equal to the first and second temperatures based on the first and second temperatures, such that heater resistance may be determined for heater temperatures not equal to the first and second temperatures. Following 308, method 300 ends.

The resistance-temperature transfer function determined according to method 300 may be used to accurately control an oxygen sensor heater, thus enabling accurate control of the oxygen sensor and desired sensing.

FIG. 4 shows a flowchart illustrating a method 400 of determining an impedance setpoint of an oxygen sensor. Method 400 may be employed to determine an impedance setpoint whose application results in a desired sensor temperature for oxygen sensor 200 (FIG. 2), for example. In some examples, method 400 may be employed to update an existing impedance setpoint, while in other examples, the method may be employed to derive a new impedance setpoint.

At 402 of method 400, it is determined whether the temperature of the oxygen sensor is at a desired sensor temperature. The desired sensor temperature may be an operational temperature at which the oxygen sensor provides desired sensing, for example. In some examples, the oxygen sensor temperature may be determined based on the resistance of its associated heater—for example, a resistance-temperature transfer function of the heater may be used to obtain a temperature corresponding to the resistance of the heater. The transfer function may be determined according to method 300, for example. If used, an adjustment may be made to the heater temperature in some examples to account for differences in thermal conditions between the heater and the oxygen sensor (e.g., a sensor element or cell of the sensor). The adjustment may include a thermal gradient factor, for example. If it is determined that the oxygen sensor is not at the desired sensor temperature (NO), method 400 returns to 402. If it is determined that the oxygen sensor is at the desired sensor temperature (YES), method 400 proceeds to 404.

At 404 of method 400, the impedance of a sensor element of the oxygen sensor is determined. The sensor element may be a sensing cell (e.g., sensing cell 226 of FIG. 2) or a pumping cell (e.g., pumping cell 228 of FIG. 2) of the oxygen sensor. The impedance of the sensor element may be determined as described above with reference to FIG. 2.

At 406 of method 400, and impedance setpoint is set to the sensor element impedance determined at 404. The impedance setpoint may be used to control the oxygen sensor such that, when employed in controlling the sensor, causes the oxygen sensor to assume a desired sensor temperature (e.g., operational temperature). Because the impedance setpoint is set to the impedance corresponding to the desired sensor temperature, application of the impedance setpoint in controlling the oxygen sensor enables the sensor to achieve the desired sensor temperature.

The impedance setpoint determined according to method 400 may be used to accurately control an oxygen sensor, enabling accurate control of the oxygen sensor and desired sensing. In some examples, the resistance-temperature transfer function determined via method 300 of FIG. 3 may be used to determine heater temperature and/or oxygen sensor temperature. Responsive to determining that the oxygen sensor temperature corresponds to a desired sensor temperature (e.g., a light-off temperature), the oxygen sensor impedance may be measured and set as an impedance setpoint on which oxygen sensor (and heater) control may be based— for example, the output of the heater may be controlled such that the oxygen sensor exhibits the impedance setpoint, in turn imbuing the oxygen sensor with the desired sensor temperature.

FIG. 5 shows a plot 500 illustrating determination of a resistance-temperature transfer function for an oxygen sensor heater. Particularly, plot 500 shows a nominal resistance-temperature transfer function 502 and an updated resistance-temperature transfer function 504. Transfer function 502 may have been determined for a non-aged oxygen sensor, for example, while transfer function 504 may have been determined for the same oxygen sensor in an aged state, or, for a different oxygen sensor exhibiting significant part-to-part variability. Generally, transfer function 504 outputs greater temperatures for resistance inputs relative to transfer function 502, though it will be appreciated that the difference in functional forms of the transfer functions is merely an example and is not intended to be limiting. One or both of transfer functions 502 and 504 may have been determined according to method 300 of FIG. 3, for example. In the depicted example, a temperature 506 is determined via transfer function 504 based on a sampled resistance 505 of the oxygen sensor heater. Temperature 506 may be used to control the oxygen sensor and its heater as described herein.

FIG. 6 shows a plot 600 illustrating determination of an impedance setpoint for an oxygen sensor. Particularly, plot 600 shows a nominal impedance-temperature relation 602 illustrating how the impedance of the oxygen sensor (e.g., sensor element) varies with temperature in a non-aged oxygen sensor, and an altered impedance-temperature relation 604 illustrating how the impedance of the oxygen sensor varies with temperature in an aged state and/or when imbued with significant part-to-part variability. Generally, an aged oxygen sensor may exhibit higher impedances for a given temperature relative to a non-aged oxygen sensor. In the depicted example, determination of an updated impedance setpoint with which the oxygen sensor may be controlled is desired so that a desired sensor temperature may be achieved when controlling the sensor with the updated impedance setpoint. Accordingly, a determination is made as to whether the oxygen sensor temperature corresponds to the desired sensor temperature. This determination may be made based on the heater resistance—for example and with reference to FIG. 5, temperature 506 may be the desired sensor temperature determined according to updated resistance-temperature transfer function 504. As such, transfer function 504 may be used to determine whether the oxygen sensor temperature corresponds to the desired sensor temperature. When it is determined that this correspondence has been achieved, the instant oxygen sensor impedance (e.g., sensor element impedance) is measured and set as the updated impedance setpoint 606 such that controlling the oxygen sensor according to the updated impedance setpoint results in the desired sensor temperature. As can be seen in FIG. 6, updated impedance setpoint 606 is greater than a previously determined, non-updated impedance setpoint corresponding to nominal impedance-temperature relation 602 and associated with temperature 506.

It will be appreciated that plots 500 and 600, of FIGS. 5 and 6 respectively, are provided as examples and are not intended to be limiting in any way. Particularly, the functional forms and values shown therein are exemplary.

FIG. 7 shows a flowchart illustrating a method 700 of controlling the voltage supplied to an oxygen sensor heater. Method 700 may be employed to control the supply voltage of heater 207 of oxygen sensor 200, both of FIG. 2, for example.

At 702 of method 700, the temperature of the heater is determined via a resistance-temperature transfer function. The resistance-temperature transfer function may be determined according to method 300 of FIG. 3, for example. A sampled resistance of the heater may be supplied to the resistance-temperature transfer function to obtain a corresponding heater temperature indicative of the instant temperature of the heater, for example.

At 704 of method 700, a desired heater temperature is determined. The desired heater temperature may be predetermined, and, as such, determination of the desired heater temperature may include retrieving the desired temperature from memory. The desired heater temperature may be a temperature at which the heater heats the oxygen sensor to a sufficient degree so as to bring the temperature of the oxygen sensor to a desired sensor temperature (e.g., light-off temperature of the oxygen sensor) at which the oxygen sensor provides desired sensing. In some examples, the desired heater temperature may correspond to the desired oxygen sensor temperature. In other examples, a difference between the desired heater and sensor temperatures may exist—for example, due to the difference in their physical locations. As such, in these examples determination of the desired heater temperature may include determining the desired oxygen sensor temperature and applying a thermal gradient factor to the desired sensor temperature to determine the desired heater temperature, the thermal gradient factor accounting for this difference in thermal conditions between the physical locations.

At 706 of method 700, the voltage supplied to the heater is adjusted based on the difference between the heater temperature determined at 702 and the desired heater temperature determined at 704. Thus, in some implementations method 700 may enable closed loop control of the heater temperature responsive to the desired heater temperature and its instant temperature. By basing determination of the heater temperature on the resistance-temperature transfer function, the heater temperature may be accurately controlled to the desired heater temperature, as the resistance-temperature function may be continually updated to enable the heater temperature to be accurately determined throughout the operational life of the heater. Following 706, method 700 ends. It will be appreciated, however, that method 700 may be performed on an iterative basis under select conditions that enable closed loop control of the heater.

FIG. 8 shows a flowchart illustrating a method 800 of determining one or more engine operating parameters based on output from an oxygen sensor. Method 800 may be employed to determine one or more engine operating parameters based on output from oxygen sensor 200 of FIG. 2, for example.

At 802 of method 800, the impedance of the oxygen sensor is determined. The oxygen sensor impedance may be determined as described above with reference to FIG. 2, and may include determining the impedance of a sensor element (e.g., sensing cell, pumping cell) of the oxygen sensor.

At 804 of method 800, an impedance setpoint of the oxygen sensor is determined. The impedance setpoint may be a desired sensor impedance; when the oxygen sensor impedance is equal to the desired sensor impedance, the oxygen sensor may have reached a desired sensor temperature, as the sensor impedance may be proportional to the sensor temperature. The impedance setpoint may be determined via method 400 of FIG. 4, for example. In other examples, a predetermined impedance setpoint may be retrieved from memory.

At 806 of method 800, the voltage supplied to an oxygen sensor heater in thermal communication with the oxygen sensor is adjusted based on a difference between the sensor impedance determined at 802 and the impedance setpoint determined at 804. Thus, in some examples, method 800 may enable closed loop control of the oxygen sensor responsive to the impedance setpoint and its instant impedance. By adjusting the heater supply voltage in this way, the impedance setpoint, and thus the desired sensor temperature, may be achieved by the oxygen sensor.

At 808 of method 800, one or more engine operating parameters are determined based on output from the oxygen sensor when operating at the impedance setpoint. The one or more operating parameters may include AFR in exhaust gas, alcohol (e.g., ethanol) content in a gas stream, and ambient humidity, for example. One or more additional operating parameters may then be adjusted by the control system based on these initially determined operating parameters—e.g., spark timing, injector timing, cam timing, etc. In this way, the one or more engine operating parameters determined at 808 may be accurately determined by operating the oxygen sensor at appropriate temperatures that enable desired sensing, which is in turn enabled by accurately controlling the oxygen sensor heating and maintaining an accurate impedance setpoint. As such, emissions may be reduced, and fuel economy and vehicle drivability increased.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method of operating an oxygen sensor including a heater, comprising:
    sampling a first heater resistance of the heater at a first temperature; and
    generating a resistance-temperature transfer function relating heater resistance to heater temperature based on the first heater resistance and a second heater resistance of the heater at a second temperature, the second temperature different from the first temperature, the first heater resistance sampled upon a vehicle on event after engine inactivity.

2. The method of claim 1, further comprising controlling the heater based on the resistance-temperature transfer function.

3. The method of claim 1, wherein determining the resistance-temperature transfer function includes extrapolating heater resistance for heater temperatures not equal to the first and second temperatures based on the first and second heater resistances, the method further comprising adjusting an actuator in response to the resistance-temperature transfer function.

4. The method of claim 1, wherein the first temperature is an ambient temperature, and
wherein the second temperature is absolute zero.

5. The method of claim 1, wherein the second heater resistance is based on a material composition of the heater.

6. The method of claim 1, wherein the second heater resistance is predetermined.

7. The method of claim 1, wherein the first heater resistance is sampled upon vehicle key-on after expiration of a threshold duration of engine inactivity.

8. The method of claim 7, wherein, after expiration of the threshold duration of engine inactivity, an engine temperature and the heater temperature are both substantially at ambient temperatures.

9. The method of claim 1, further comprising:
determining whether the heater temperature corresponds to a desired temperature based on the resistance-temperature transfer function;
responsive to determining that the heater temperature corresponds to the desired temperature, sampling an impedance of the oxygen sensor; and
setting an impedance setpoint to the sampled impedance.

10. The method of claim 9, further comprising controlling the oxygen sensor based on the impedance setpoint.

11. The method of claim 1, wherein the second heater resistance is sampled at the second temperature, and
wherein the second temperature is an operational temperature of the oxygen sensor.

12. A method of controlling an oxygen sensor, comprising:
responsive to determining that a temperature of the oxygen sensor corresponds to a desired temperature, determining an impedance of the oxygen sensor;
setting an impedance setpoint to the determined impedance; and
adjusting the oxygen sensor so that the impedance of the oxygen sensor corresponds to the impedance setpoint, wherein the correspondence of the oxygen sensor temperature to the desired temperature is determined based on a first and a second resistance of a heater in thermal communication with the oxygen sensor, the first heater resistance sampled upon a vehicle on event after engine inactivity, the first resistance different than the second resistance.

13. The method of claim 12, wherein adjusting the oxygen sensor so that the impedance of the oxygen sensor corresponds to the impedance setpoint brings the oxygen sensor temperature to the desired temperature.

14. The method of claim 12, wherein the impedance of the oxygen sensor is an impedance of an oxygen sensor element.

15. The method of claim 12, wherein the desired temperature is a temperature of the oxygen sensor at which the oxygen sensor provides sensing.

16. A method of operating an oxygen sensor including a heater, comprising:
sampling a heater resistance of the oxygen sensor heater at a first temperature;
determining a resistance-temperature transfer function relating heater resistance to heater temperature based on the sampled heater resistance and a predetermined heater resistance of the oxygen sensor heater at a second temperature, the second temperature different from the first temperature, the first heater resistance sampled upon a vehicle on event after a threshold duration of engine inactivity;
responsive to determining that a temperature of the oxygen sensor corresponds to a desired temperature based on the resistance-temperature transfer function, determining an impedance of the oxygen sensor; and
setting an impedance setpoint to the determined impedance.

17. The method of claim 16, wherein determining the correspondence of the oxygen sensor temperature to the desired temperature includes determining the heater temperature based on the resistance-temperature transfer function and applying a thermal gradient factor to the heater temperature to determine the oxygen sensor temperature, the thermal gradient factor accounting for a difference in thermal conditions between the heater and the oxygen sensor.

18. The method of claim 16, further comprising controlling the oxygen sensor so that the impedance of the oxygen sensor corresponds to the impedance setpoint.

19. The method of claim 18, wherein controlling the oxygen sensor so that the impedance of the oxygen sensor corresponds to the impedance setpoint includes controlling the heater to achieve the impedance setpoint.

* * * * *